United States Patent [19]

Finch

[11] Patent Number: 4,848,351

[45] Date of Patent: Jul. 18, 1989

[54] MEDICAL ELECTRODE ASSEMBLY

[75] Inventor: Gary J. Finch, Santa Ana, Calif.

[73] Assignee: Sentry Medical Products, Inc., Santa Ana, Calif.

[21] Appl. No.: 159,171

[22] Filed: Feb. 23, 1988

Related U.S. Application Data

[63] Continuation-in-part of Ser. No. 21,451, Mar. 4, 1987, abandoned.

[51] Int. Cl.⁴ .................................................. A61B 5/04
[52] U.S. Cl. ............................. 128/640; 128/DIG. 15
[58] Field of Search ................................. 128/639–641, 128/644, 798, 802, 803, DIG. 15

[56] References Cited

U.S. PATENT DOCUMENTS

| | | | |
|---|---|---|---|
| 3,542,010 | 11/1970 | Love | 128/644 |
| 3,572,323 | 3/1971 | Yuan | 128/640 |
| 4,072,145 | 2/1978 | Silva | 128/644 |
| 4,239,046 | 12/1980 | Ong | 128/640 |
| 4,522,211 | 6/1985 | Bare et al. | 128/640 |

Primary Examiner—Lee S. Cohen
Attorney, Agent, or Firm—Christie, Parker & Hale

[57] ABSTRACT

A medical electrode assembly for use with a medical device for monitoring electric impulses from a patient, comprising an electrically conductive lead wire, a connector electrically joined to a first end portion of said lead wire, electrically conductive hook fasteners electrically secured to a second end portion of said lead wire, and an electrode comprising a top portion having electrically conductive loops for removably fastening said hook fasteners thereto, and a bottom portion having an electrically conductive medium in contact with the patient's skin and the top portion of the electrode, and an adhesive for removably securing said electrode to the skin.

4 Claims, 1 Drawing Sheet

MEDICAL ELECTRODE ASSEMBLY

CROSS-REFERENCE TO RELATED APPLICATIONS

This application is a continuation-in-part of Ser. No. 07/021,451, filed Mar. 4, 1987, now abandoned.

BACKGROUND OF THE INVENTION

The invention relates to a medical electrode assembly for use with medical devices used for monitoring electrical currents produced by the body.

Medical electrodes are well known in the art and vary considerably in their structure and method of manufacture. They generally comprise an electrode designed to be applied and held to the skin of a patient, a conductive lead wire removably, electrically attached to the electrode at one end thereof, and an electrical connector at the other end of the lead wire for making an electrical connection with a medical monitoring device. Conventional medical electrodes are relatively complex in their structure and method of manufacture. Many of these electrodes have relatively hard, bulky components which make them uncomfortable to the patient. Conventional medical electrodes are generally limited to one lead wire so that the electrode may only be used with one monitoring device. If more than one monitoring device is required for a patient, a separate electrode is generally required for each monitoring device.

SUMMARY OF THE INVENTION

The present invention eliminates the aforesaid problems associated with prior medical electrodes by providing an electrode assembly which is relatively simple in its structure and method of manufacture. The electrode assembly of the present invention has no hard components, is relatively small and flexible in size, and is comfortable to the patient. The electrode assembly of the present invention may also be used to provide multiple connections to a number of monitoring devices and thus eliminates the need for a separate electrode for each monitoring device.

These advantages and benefits are realized from the medical electrode assembly of the present invention which is generally comprised of an electrically conductive lead wire, a conductor electrically joined at a first end portion of said lead wire, an electrically conductive hook fastener electrically secured to a second end portion of the lead wire, and an electrode comprising a top portion having electrically conductive loops for removably fastening the hook fasteners thereto, and a bottom portion having an electrically conductive adhesive in contact with the patient's skin and the top portion of the electrode.

A preferred embodiment of the present invention is described in the following description and illustrated in the accompanying drawings.

DESCRIPTION OF THE PREFERRED EMBODIMENT

Figure 1:
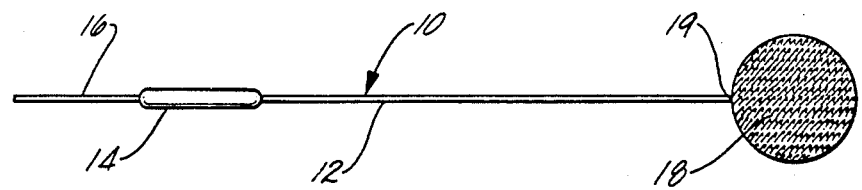
FIG. 1 is a bottom view of the electrically conductive lead wire used with the medical electrode assembly of the present invention.
Figure 2:
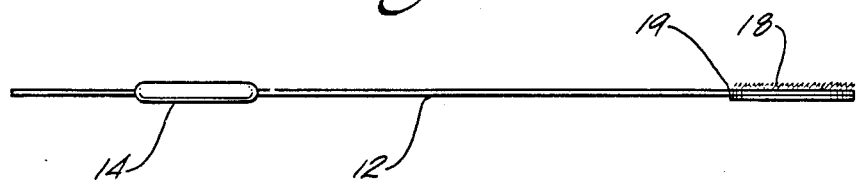
FIG. 2 is a side view of the lead wire illustrated in FIG. 1.

As illustrated in FIGS. 1 and 2 the medical electrode assembly of the present invention comprises an electrically conductive lead wire 10 having a connector 14 electrically joined to a first end portion 16 of the lead wire. Electrically conductive hook fasteners 18 are secured to a second end portion of the lead wire 19.

Figure 3:
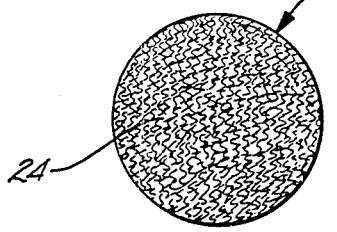
FIG. 3 is an enlarged view of the electrode used with the medical electrode assembly of the present invention.
Figure 4:
FIG. 4 is a side view of the electrode illustrated in FIG. 3.

The electrode 20 for contacting the skin is illustrated in FIGS. 3 and 4. The electrode 20 comprises a top portion having electrically conductive loops 24 for removably fastening said hook fasteners 18 on the lead wire when applied thereto, and a bottom portion having an electrically conductive adhesive suitable for removably securing the electrode to the patients skin.

The lead wire may be any conventional electrically conductive wire used with medical electrodes and is generally provided with an insulated coating thereon. The electric connector 14 is of conventional manufacture and has typically a 0.08 inch diameter male pin 16 which is designed to fit into most monitoring devices.

The electrically conductive hook fasteners 18 are generally the hook portion of "Velcro" type fasteners and are secured to the second end portion 19 by conventional means. These hook fasteners 18 may be made of conventional material such as fabric and nylon, and made conductive by coating with a conductive material such as silver. Alternatively, the hook fasteners may be made conductive by manufacture from a conductive material such as finely woven metals.

The conductive loop fasteners 24 forming the top portion 22 of the electrode 20 for application to the patient's skin, may be manufactured from the same materials as the hook fasteners described above, and are coated with a conductive material such as silver. The loop fasteners have a nonloop side which is coated with a conductive ink containing a mixture of silver and silver chloride resulting in a flexible plastic film which does not crack when the electrode 20 is flexed.

The silver-silver chloride coating enhances the electrical properties of the medical electrode assembly. The ink which forms said flexible plastic film is conventional in the art and may be an ink made from polyurethane and the like.

Figure 5:
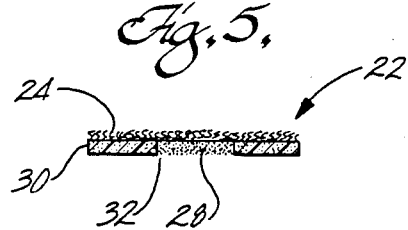
FIG. 5 is a side view of an alternative electrode.

The electrically conductive adhesive forming the bottom portion 26 of the electrode 20 is selected from materials such as a hydrogel, which will bind to the top portion 22 of the electrode 20 to form a unitary structure and also provide the necessary electrically conductive adhesive surface for securing the electrode to the patient's skin. Alternatively, as illustrated in FIG. 5, a non-adhesive conductive gel 28 may also be used provided an adhesive is used therewith such as an adhesive donut 30 having its center portion 32 filled with said conductive gel. In this alternative, the donut 30 is provided with adhesive on each side so it may conform to and be secured to the top portion of the electrode and to the patient's skin, and form a center space 32 to receive the conductive gel 28. A removable backing (not shown) is provided across said donut 30 and gel 28 to prevent leakage or drying out of the gel 28 during storage. The presence of the flexible plastic ink coating of silver-silver chloride will prevent the gel from drying out through the top of the electrode, and will control the half cell potential which develops at the junction of the conductive gel and the conductive loops.

Electrical contact between the electrode 20 and the monitoring device is achieved by pressing the electrically conductive hook fasteners 18 on the second end portion of the lead wire 10, top the electrically conductive loops 24 on the top portion of the electrode 20. The connector 14 is inserted into the monitoring device to complete the electrical circuit.

The electrode 20 may have one row of conductive loops for connecting with one lead wire, or the entire surface of the electrode 20 may be provided with conductive loops so that may number of lead wires may be attached thereto and connected with any number of monitoring devices.

At the conclusion of the monitoring session, the lead wire may be removed from the electrode by pulling the hook fasteners off of the loops in the same manner that a conventional "Velcro" hook and loop fasteners are removed from each other. The electrode may also be removed from the patient's skin and applied to another portion of the patient's body provided there is sufficient adhesion and conductivity remaining in the bottom portion of the electrode.

The electrode assembly of the present invention has been described in terms of providing hook fasteners on the lead wire and loop fasteners on the top portion of the electrode. However, this order may be reversed and the hook fasteners may be provided on the top portion of the electrode and the loop fasteners may be provided on the lead wire.

While the embodiment of the invention set forth herein for purposes of disclosure is considered to be preferred, it is to be understood that this invention is intended to cover all changes in modifications in the disclosed embodiment which fall within the spirit and scope of the invention.

What is claimed is:

1. A medical electrode assembly for use with a medical device for monitoring electric currents from a patient, comprisng:
   an electrically conductive lead wire;
   a connector electrically joined to a first end portion of said lead wire;
   electrically conductive hook or loop fasteners electrically secured to a second end portion of said lead wire, said fasteners having a loop or hook side and an underside where loops or hooks are not present; and
   an electrode comprising a top portion having electrically conductive loop or hook fasteners removably connected with hook or loop fasteners, and a bottom portion having an electrically conductive medium for contacting the patient's skin, said hook or loop fasteners of said electrode being made of a non-conductive material coated with silver and having a non-loop or non-hook side which forms the bottom portion of said electrode and is coated with a conductive ink containing a mixture of silver and silver chloride to produce a flexible conductive plastic film which does not crack when the electrode is flexed.

2. The medical electrode assembly of claim 1 wherein an adhesive for removably securing said electrode to the patient's skin is provided on the bottom portion thereof.

3. The medical electrode assembly of claim 1 wherein said electrically conductive medium is hydrogel.

4. The medical electrode assembly of claim 1 wherein an adhesive donut, having adhesive on each side, is secured to the bottom portion of said electrode with one of said adhesive sides, and provides an adhesive on the other side of the donut for securing to a patient's skin, said donut having a center space receiving said conductive medium in the form of a conductive gel.

* * * * *